United States Patent [19]
Dimeff

[11] 3,953,734
[45] Apr. 27, 1976

[54] NULLING DEVICE FOR DETECTION OF TRACE GASES BY NDIR ABSORPTION

[75] Inventor: John Dimeff, San Jose, Calif.

[73] Assignee: The United States of America as represented by the Administrator of the National Aeronautics and Space Administration, Washington, D.C.

[22] Filed: Nov. 22, 1974

[21] Appl. No.: 526,438

[52] U.S. Cl............................. 250/343; 250/344; 250/432 R
[51] Int. Cl.².................................... G01N 21/26
[58] Field of Search................. 250/343, 344, 432

[56] References Cited
UNITED STATES PATENTS

| 3,227,873 | 1/1966 | Liston | 250/344 |
|---|---|---|---|
| 3,679,899 | 7/1972 | Dimeff | 250/343 |

*Primary Examiner*—Davis L. Willis
*Attorney, Agent, or Firm*—Darrell G. Brekke; Armand G. Morin; John R. Manning

[57] ABSTRACT

A non-dispersive gas analyzing apparatus is described having a first chamber for containing a first gas, the density of which it is desired to determine. A source of radiant energy is provided for passing radiant energy through the first chamber. Modulation means are provided for modulating the radiant energy passing through the first chamber by modulating the volume of the chamber at the acoustic resonance frequency of the first gas and the chamber. Signal generating means including a second chamber for containing a gas which is heated by radiant energy emerging from the first chamber and a microphonic means responsive to the resulting pressurization in the second chamber is provided for generating a signal having a frequency and amplitude corresponding to the modulation of the radiant energy in the first chamber. In one embodiment this signal is used to modulate in phase opposition radiant energy passing through an intermediate gas-filled third chamber so as to cancel in the second chamber the effects of the modulation in the first chamber. In a second embodiment this signal is used to modulate in phase opposition the intensity of the radiant energy emerging from the energy source so as to cancel in the second chamber the effects of the modulation in the first chamber. Output means are further provided responsive to the amplitude of the signal generated by the signal generating means and the amplitude of the modulation in the first chamber for providing an output proportional to the density of the gas in the first chamber.

12 Claims, 2 Drawing Figures

NULLING DEVICE FOR DETECTION OF TRACE GASES BY NDIR ABSORPTION

The invention described herein was made by an employee of the United States Government and may be manufactured and used by or for the Government for governmental purposes without the payment of any royalties thereon or thereafter.

BACKGROUND OF THE INVENTION

Complex molecules generally have spectra in the infrared which are rich in detail and specific to the molecule, thereby providing one of the best signatures by which to identify the particular molecule. Various techniques have been developed to measure the infrared spectral absorption or emission characteristic of unknown gases as a means of identifying and quantifying its composition. Advantages and disadvantages of the various methods are described briefly in the specification of U.S. Pat. No. 3,679,899, issued to applicant July 25, 1972. That disclosure, in turn, described a means of reducing the limitations on existing NDIR gas detection devices by providing a means of increasing the specificity based on a technique which could be used with essentially all non-symmetrical molecules of modest size. The method it described, however, required the use of electronic equipment and optical detectors that were more complex than most because the absorption-absorption heterodyning signal on which it was based was inherently small.

SUMMARY OF THE INVENTION

In view of the foregoing, a principal object of this invention is a non-dispersive gas analyzing apparatus for extending the absorption-absorption technique in a manner that will preserve its advantages while eliminating the disadvantages associated with inherently small signals.

Another object of the invention is a non-dispersive gas analyzing apparatus which operates on the optical absorption signal itself, as opposed to the small non-linearity in that signal as employed in an absorption-absorption heterodyning technique.

In accordance with these objects there is described two embodiments of the present invention. In the first embodiment, there is provided three chambers for containing a first, a second and a third gas. Radiant energy is passed serially through the first and second chambers and into the third chamber. The radiant energy in the first chamber is modulated at a frequency and amplitude corresponding to the acoustic resonance frequency of the first gas and first chamber. The radiant energy in the second chamber is modulated at the frequency of modulation of the radiant energy in the first chamber but at an amplitude in phase opposition thereto. The magnitude of the amplitude of the modulation of the radiant energy in the second chamber is determined by the magnitude of the heating and resulting pressurization of the third gas in the third chamber caused by the modulation of the radiant energy in the first chamber so as to, in effect, null out in the third chamber the effects of the modulation of the radiant energy in the first chamber. The amplitude of the modulation of the radiant energy in the first and second chambers and then used for providing an output which is proportional to the density of the gas in the first chamber.

In the second embodiment, the second chamber and its associated modulation apparatus are omitted. The third chamber receives the radiant energy directly from the first chamber and, together with its associated circuitry, provides a signal for modulating the intensity of the radiant energy emerging from the radiant energy source in phase opposition to the modulation of the radiant energy in the first chamber so as to, in effect, null out in the third chamber the effects of the modulation of the radiant energy in the first chamber.

By means of apparatus, according to the present invention, there is provided the advantages of simplicity, reduced cost and increased threshold sensitivity.

DESCRIPTION OF THE DRAWINGS

The foregoing and other objects, features and advantages of the present invention will be apparent from the following detailed description and accompanying drawings in which.

DETAILED DESCRIPTION

Figure 1:
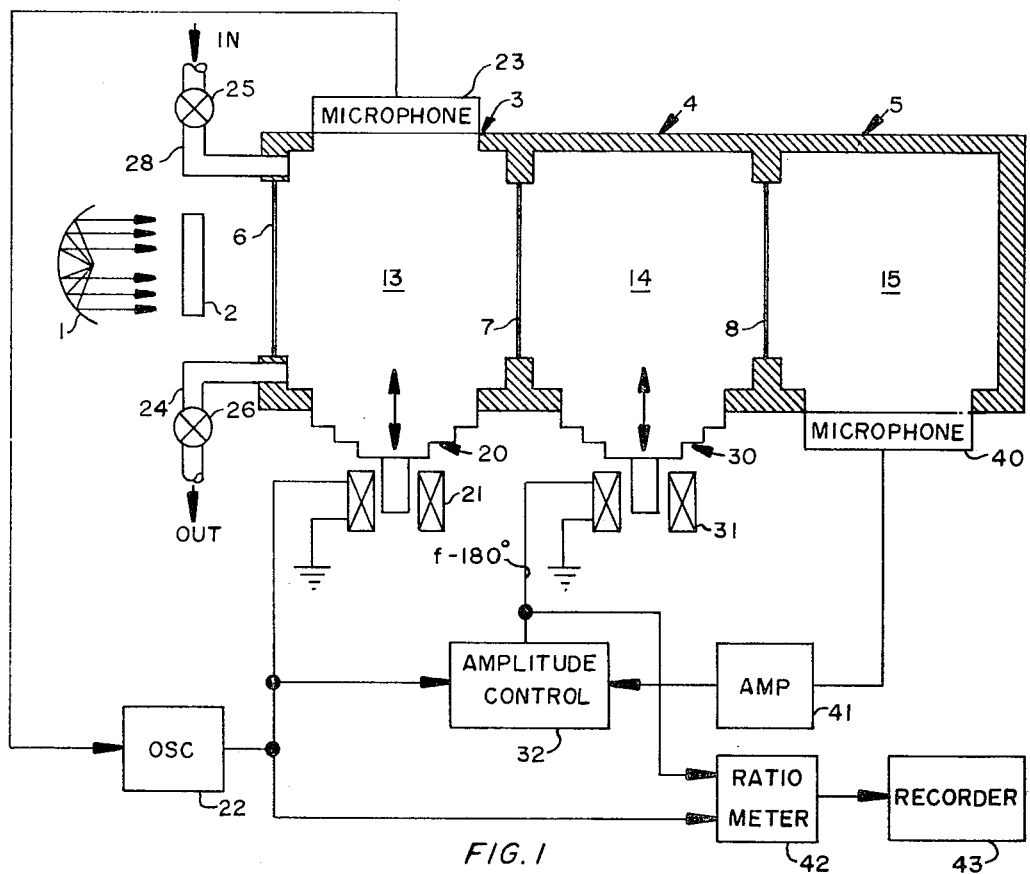
FIG. 1 is a schematic diagram of a simplified embodiment of the present invention.

Referring to FIG. 1, there is provided in a first embodiment of the present invention, a light source 1 for providing broad-band radiant energy as illustrated by a plurality of parallel arrows. To the right of source 1, there is provided a transmission filter 2, and a plurality of chambers designated generally as 3, 4 and 5, having a plurality of windows 6, 7 and 8 for passing radiant energy from the source 1. Chambers 3, 4 and 5 form, respectively, a plurality of independent gas-containing spaces 13, 14 and 15. In one wall portion of chamber 3 there is provided a flexible diaphragm or bellows 20 which is electromagnetically driven by a solenoid 21 coupled to an oscillator 22 for periodically varying the volume of the chamber. Opposite bellows 20 in a second wall of chamber 3 is a microphone 23 for providing a signal corresponding to pressure variations in a gas in chamber 3 when the volume of the chamber is varied. Microphone 23 is coupled to the oscillator 22 for controlling the frequency of the oscillator 22 to provide a maximum amplitude signal output according to the pressure amplification obtained as a result of an acoustic resonance resulting from the design of chamber 3 and the acoustic properties of the gas contained therein. There is further provided in chamber 3, a pair of pipes 28 and 24 with conventional in-line valve means 25 and 26, respectively, for controlling gas flow into and out of the space 13.

Chamber 4 is positioned intermediate chambers 3 and 5 and is provided in one wall portion with a flexible diaphragm or bellows 30 coupled electromagnetically to a solenoid 31. Bellows 30 is provided to periodically vary the volume of the chamber 4. Solenoid 31 is coupled to the oscillator 22 through an amplitude control circuit 32. Amplitude control circuit 32 controls the amplitude of the signal driving the solenoid. In chamber 5 there is provided a microphone 40. Microphone 40 is responsive to the pressurization of gas in the space 15 for outputting a signal to an amplifier 41. Amplifier 41 is coupled to amplitude control circuit 32 and with conventional phase shifting circuits outputs a signal for controlling the amplitude and phase of the output of amplitude control circuit 32. Coupled to the output of control circuit 32 and oscillator 22 is a ratio meter 42 and a recorder 43 for recording a signal proportional to the ratio of the two outputs.

In operation, unknown gas enters space 13 of chamber 3 through input pipe 28 and exits through output pipe 24 in either a continuous flow or as a batch sample, depending on the apparatus and application in which it is used. A measured sample of the gas whose presence in chamber 3 is to be detected is contained in space 14 totally enclosed and sealed within the chamber 4 and mixed with various optically inert gases such as nitrogen and helium so that the velocity of sound of the combined gases contained in chamber 4 is the same as that of the gas expected in chamber 3. In chamber 5 there is provided a gas mixture similar to that within chamber 4, but perhaps of different proportions, which is sealed within the chamber the same as the gas in chambers 3 and 4. Broad-band light from source 1 is filtered by the transmission filter 2 which passes only that portion of the radiation in which absorption lines for the gas of interest are known to occur. Also eliminated by appropriately selected absorbing gases in filter 2 are selected absorption lines which are known to overlap particularly strong lines of any known interfering gases. As the radiation traverses space 13, the intensity of the radiation will be modified by the absorption signature of the gas being measured, that modification being modulated by the variation of the density of the gas in space 13 as caused by driver bellows 20. In the absence of any variability of the gas density in space 14, the intensity of the spectral absorption lines of interest will be reduced somewhat during its passage through space 14, both the average value and the fluctuations being reduced in the same proportion. The energy in the absorption spectrum of interest will again be absorbed by the gas contained within space 15 producing a slight and constant heating and pressurization due to the steady component, and a dynamic component due to the fluctuation. Since the dynamic component of pressure occurs at the acoustic resonance frequency of the gas space 15 in chamber 5, it will be amplified thereby. Microphone 40, then, produces an output proportional to the fluctuating component of the spectral lines of interest, and proportional to the product of the fractional pressure fluctuations in space 13 and the fractional density of the desired gas in space 13. The signal from microphone 40 is amplified by amplifier 41 and phased in such a manner that the product of the output of amplifier 41 and the output of oscillator 22, as developed by amplifier control circuit 32 and delivered to solenoid 31, is in phase opposition to the drive supplied to solenoid 21. As the signal from microphone 40 increases, therefore, the signal driving solenoid 31 increases in opposition to amplitude control circuit 32, modifying the density in space 14 in opposition to the density fluctuation in space 13, and tends to produce a fluctuating absorption of the radiation therethrough only within the spectral lines of interest, said absorption tending to cancel that introduced by the gas in space 13. With the gains and phases of space 15, microphone 40, amplifier 41, amplitude control circuit 32 and solenoid 31 corrected and adjusted in accordance with well known feedback theory, the canceling effect of absorption in space 14 on absorption in space 13 increases until the relationship $$\frac{\Delta P_{13}}{P_{13}} \rho_{13} = \frac{\Delta P_{14}}{P_{14}} \rho_{14}$$

is satisfied; where $\Delta P_x/P_x$ is the fractional pressure change in space 13 or 14 as produced by bellows 20 or 30, respectively.

$\rho_{13}$ is the unknown absolute density of the desired gas in space 13 and $\rho_{14}$ is the known density of the desired gas in space 14.

The density of the desired gas in the unknown sample within space 13 is then simply derived by the equation $$\rho_{13} = \frac{\frac{\Delta P_{14}}{P_{14}}}{\frac{\Delta P_{13}}{P_{13}}} \rho_{14}$$

and since $\Delta P_{14}/P_{14}$ and $\Delta P_{13}/P_{13}$ are proportional to $V_{31}$ and $V_{21}$ (the driving signals supplied to solenoid 31 and solenoid 21, respectively)

$$\rho_{13} = \frac{V_{31}}{V_{21}} \rho_{14}$$

Accordingly, meter 42 computes the ratio of $V_{31}$ to $V_{21}$ and multiplies that ratio by an appropriate constant which accounts for the preselected value of $\rho_{14}$ and the relative efficiencies of the acoustic drive systems related to space 13 and 14; and provides an output proportional to the density to be measured.

Figure 2:
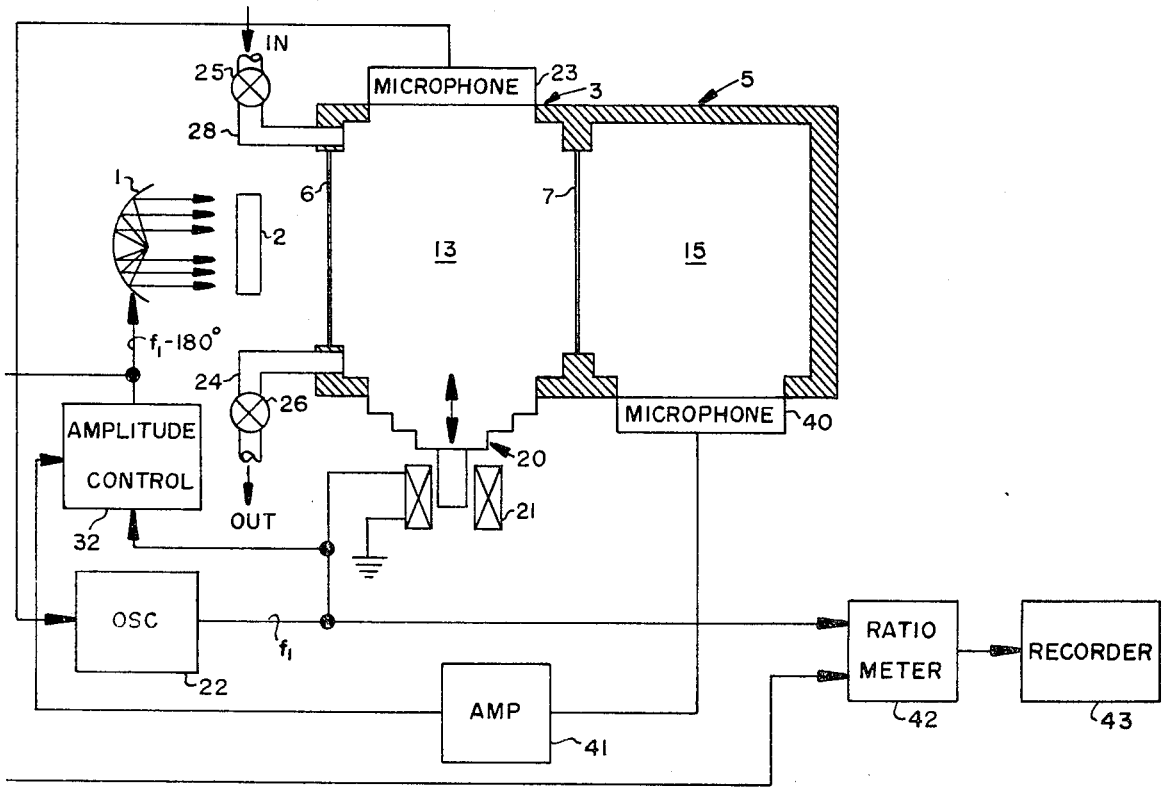
FIG. 2 is a schematic diagram of an alternative embodiment of the present invention.

Referring to FIG. 2, there is provided an alternative embodiment of the present invention wherein the chamber 4 of FIG. 1 and its associated modulation circuitry are omitted and the output of microphone 40 and the output of oscillator 22 are used to modulate the intensity of the radiant energy from the radiant energy source 1 in substantially the same manner as they are used to control the amplitude of the modulation of the radiant energy in chamber 4. In this embodiment, source 1 includes conventional means (not shown) which is coupled and responsive to the output of amplitude control circuit 32 for modulating the intensity of the radiant energy at the acoustic resonance frequency modulating the radiant energy in space 13 but in phase opposition thereto. The magnitude of the opposing modulation is such as to cancel or null out in the space 15 the effects of the modulation in space 13. As in the apparatus of FIG. 1, the ratio meter 42 is coupled to the output of oscillator 22 and the amplitude control circuit 32 for providing a signal to the recorder 43 which is proportional to the density of the gas of interest in space 13.

Refinements in the embodiments described, such as arranging the spaces 13, 14 and 15 as elements of helmholtz resonators; arranging the sensitive mechanical axes of bellows 20 and 30 and microphone 40 so as to be mutually orthogonal to minimize momentum coupling; arranging filter 2 so as to provide a segmented filter which can be repositioned to transmit energy in any of a series of preselected bands characterized by absorption spectra of several unknown gases of interest; and modifying the composition of the gases in spaces 14 and 15 to contain simultaneously samples of those several gases, thus allowing measurement of any selected one of those gases by appropriate positioning of filter 2, are all considered well within the skill of the art and obvious extensions of the embodiments described.

Accordingly, it is intended that the embodiments described are to serve merely as illustrations of preferred embodiments of the invention and that the above suggested modifications and their equivalents are considered to be clearly within the spirit and scope of the invention as hereinafter claimed.

What is claimed is:

1. A non-dispersive gas analyzing apparatus for measuring the density of a desired gas comprising:
   a chamber for containing a gas to be analyzed, said chamber having a radiant energy transmissive entrance window and a radiant energy transmissive exit window opposite said entrance window;
   means for impinging a modulated radiant energy beam on said entrance window, said beam being modulated at frequency f;
   means for modulating the radiant energy inside said chamber that has entered via said entrance window, the modulation having a frequency f and being 180 degrees out of phase with said modulated radiant energy beam; and
   means responsive to said impinging means and said modulating means for providing an output representative of the density of the desired gas contained in said chamber.

2. An apparatus according to claim 1 wherein frequency f is the acoustic resonance frequency of said chamber.

3. An apparatus as set forth in claim 2 wherein said modulation means comprises means for varying the volume of said chamber.

4. Apparatus according to claim 3 wherein said means for varying volume comprises a transducer, a bellows, and a bellows driver, said transducer being positioned within said chamber and responsive to one or more parameters of the gas in said chamber, the output of said transducer being coupled to said driver and the output of said driver being coupled to said bellows.

5. Apparatus in accordance with claim 4 wherein said modulation means includes means for varying the amplitude of modulation as a function of the radiant energy leaving said exit window from within said chamber.

6. Apparatus as set forth in claim 5 wherein said impinging means includes a radiant energy generator and means coupled to said generator for modulating the intensity of the radiant energy at frequency f.

7. A non-dispersive gas analyzing apparatus for measuring the density of a desired gas comprising:
   first and second chambers for containing gases, said first chamber adapted to contain the gas to be analyzed, said second chamber adapted to contain at least some of said desired gas;
   means for serially transmitting radiant energy through both of said chambers;
   first modulation means for modulating said radiant energy in said first chamber at frequency f;
   second modulation means for modulating said radiant energy in said second chamber at frequency f but in phase opposition to the modulation associated with said first chamber; and
   means responsive to said first and second modulation means for providing an output respresentative of the density of said desired gas contained in said first chamber.

8. An apparatus according to claim 7 wherein frequency f is the acoustic resonance frequency of said first chamber.

9. An apparatus as set forth in claim 8 wherein said first modulation means comprises means for varying the volume of said first chamber.

10. An apparatus according to claim 9 wherein said second modulation means comprises means for varying the volume of said second chamber.

11. An apparatus in accordance with claim 10 wherein said second modulation means includes means for varying the amplitude of modulation as a function of the radiant energy leaving said second chamber.

12. Apparatus according to claim 11 wherein said means for varying volume comprises a transducer, a bellows, and a bellows driver, said transducer being positioned within said first chamber and responsive to one or more parameters of the gas in said first chamber, the output of said transducer being coupled to said driver, and the output of said driver being coupled to said bellows.

* * * * *